US012582786B2

(12) United States Patent
Sutherland et al.

(10) Patent No.: US 12,582,786 B2
(45) **Date of Patent: \*Mar. 24, 2026**

(54) COMPLIANCE MONITOR FOR LOOSELY COUPLING TO AN INHALER

(71) Applicant: Adherium (NZ) Limited, Auckland (NZ)

(72) Inventors: Garth Campbell Sutherland, Auckland (NZ); Michael James Gormack, Auckland (NZ)

(73) Assignee: Adherium (NZ) Limited, Auckland (NZ)

( \* ) Notice: Subject to any disclaimer, the term of this patent is extended or adjusted under 35 U.S.C. 154(b) by 0 days.

This patent is subject to a terminal disclaimer.

(21) Appl. No.: 18/142,327

(22) Filed: May 2, 2023

(65) Prior Publication Data

US 2023/0263966 A1 Aug. 24, 2023

Related U.S. Application Data

(63) Continuation of application No. 14/129,257, filed as application No. PCT/NZ2012/000168 on Sep. 20, 2012, now Pat. No. 11,684,729.

(30) Foreign Application Priority Data

Sep. 23, 2011 (NZ) ........................................ 595367

(51) Int. Cl.
    *A61M 15/00* (2006.01)
(52) U.S. Cl.
    CPC ...... *A61M 15/008* (2014.02); *A61M 15/0071* (2014.02); *A61M 15/009* (2013.01);
    (Continued)

(58) Field of Classification Search
    CPC .......................... A61M 15/008; A61M 15/009
    See application file for complete search history.

(56) References Cited

U.S. PATENT DOCUMENTS

| | | |
|---|---|---|
| 4,817,822 A | 4/1989 | Rand et al. |
| 4,846,168 A | 7/1989 | Abiko et al. |

(Continued)

FOREIGN PATENT DOCUMENTS

| | | |
|---|---|---|
| EP | 1019125 B1 | 11/2005 |
| WO | 1999036115 A | 7/1999 |

(Continued)

OTHER PUBLICATIONS

International Search Report issued in corresponding International Application No. PCT/NZ2012/000168 dated Jan. 10, 2013.

*Primary Examiner* — Kathryn E Ditmer
(74) *Attorney, Agent, or Firm* — KENEALY VAIDYA LLP

(57) ABSTRACT

This invention relates to a compliance monitor for monitoring patient usage of a medicament delivery device, where the medicament delivery device includes a store of medicament and an actuator. The compliance monitor includes a housing adapted to enclose the medicament delivery device, and a dose counter, associated with the housing, for recording the delivery of a dose of medicament to the patient from the medicament delivery device. The arrangement and construction is such that the housing is loosely coupled to the medicament delivery device, whereby the housing is able to move relative to the medicament delivery device during the delivery of the dose of medicament, and it is this movement which actuates the dose counter, either directly or indirectly, in order to record the delivery of the dose of medicament.

15 Claims, 4 Drawing Sheets

Figure 1:
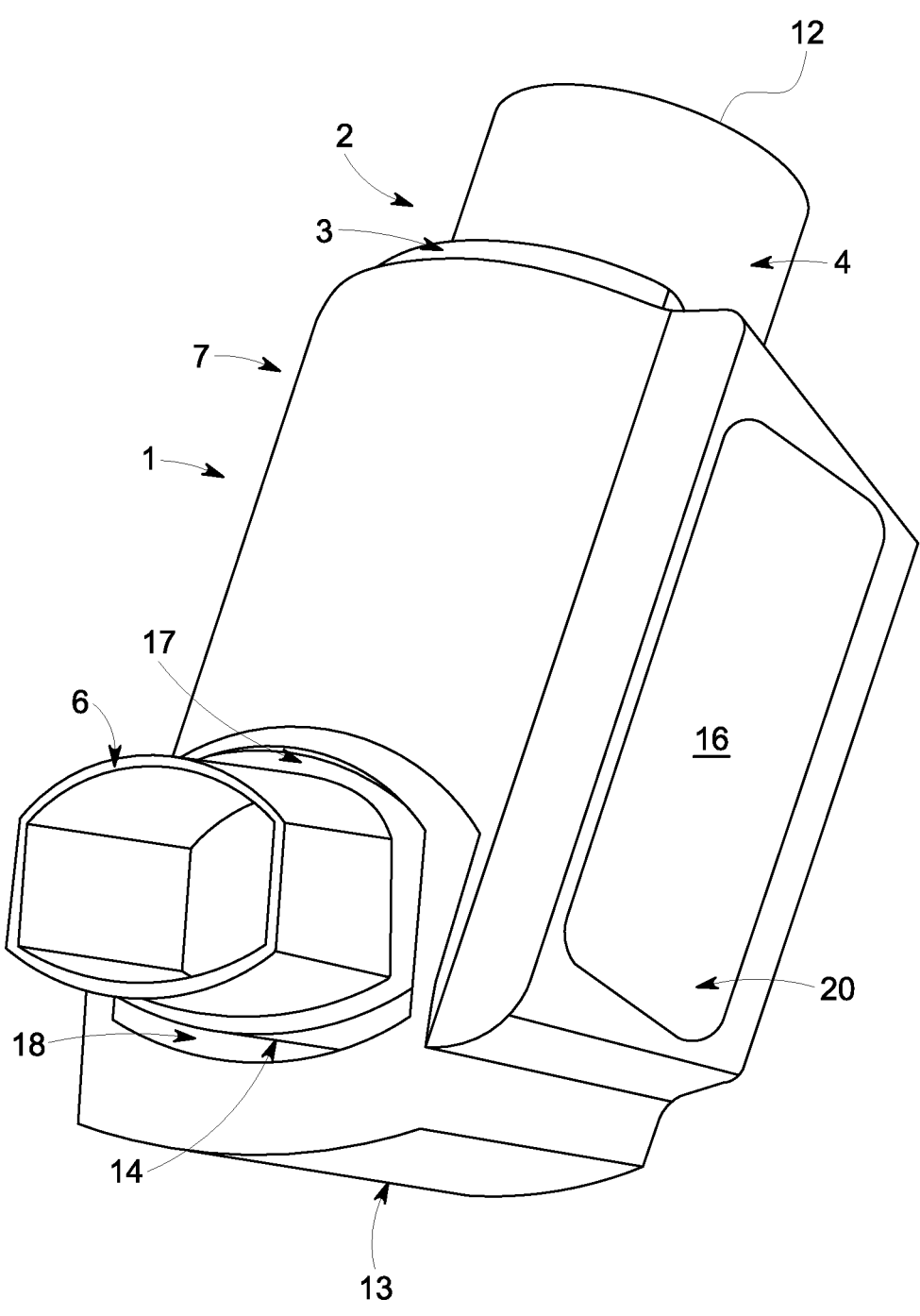

(52) U.S. Cl.
CPC ............... *A61M 2205/3368* (2013.01); *A61M 2205/3561* (2013.01); *A61M 2205/3592* (2013.01); *A61M 2205/6063* (2013.01); *A61M 2230/50* (2013.01)

(56) References Cited

U.S. PATENT DOCUMENTS

| | | | |
|---|---|---|---|
| 5,020,527 A | 6/1991 | Dessertine | |
| 5,363,842 A | 11/1994 | Mishelevich et al. | |
| 5,544,647 A | 8/1996 | Jewett et al. | |
| 5,564,414 A | 10/1996 | Walker et al. | |
| 5,730,118 A * | 3/1998 | Hermanson | A61M 15/00 128/200.14 |
| 5,809,997 A | 9/1998 | Wolf | |
| 6,202,642 B1 | 3/2001 | McKinnon et al. | |
| 6,601,582 B2 | 8/2003 | Rand et al. | |
| 6,651,651 B1 | 11/2003 | Bonney | |
| 6,958,691 B1 | 10/2005 | Anderson et al. | |
| 7,347,200 B2 | 3/2008 | Jones | |
| 8,240,301 B2 | 8/2012 | Spaargaren | |
| 8,342,172 B2 | 1/2013 | Levy et al. | |
| 8,387,614 B2 | 3/2013 | Geser | |
| 8,424,517 B2 | 4/2013 | Sutherland et al. | |
| 8,464,707 B2 | 6/2013 | Jongejan et al. | |
| 11,253,661 B2 | 2/2022 | Engelhard | |
| 2005/0028815 A1 | 2/2005 | Deaton et al. | |
| 2005/0228341 A1 | 10/2005 | Edgerley | |
| 2006/0084908 A1 * | 4/2006 | Bonney | A61M 15/009 128/200.24 |
| 2006/0130838 A1 | 6/2006 | Lee et al. | |
| 2008/0135043 A1 | 6/2008 | Lintern et al. | |
| 2008/0230057 A1 | 9/2008 | Sutherland | |
| 2009/0151723 A1 * | 6/2009 | Lang | A61M 15/008 128/203.15 |
| 2010/0192948 A1 * | 8/2010 | Sutherland | G16H 20/10 128/203.15 |
| 2010/0250280 A1 | 9/2010 | Sutherland | |
| 2010/0252036 A1 | 10/2010 | Sutherland et al. | |
| 2013/0008436 A1 | 1/2013 | Von Hollen et al. | |
| 2014/0182584 A1 | 7/2014 | Sutherland et al. | |

FOREIGN PATENT DOCUMENTS

| | | | |
|---|---|---|---|
| WO | 2006062450 A1 | 6/2006 | |
| WO | 2006126965 A1 | 11/2006 | |
| WO | WO-2011083377 A1 * | 7/2011 | ........ A61M 15/0005 |

* cited by examiner

COMPLIANCE MONITOR FOR LOOSELY COUPLING TO AN INHALER

RELATED APPLICATIONS AND PRIORITY

This application claims priority to and is a continuation patent application of U.S. patent application Ser. No. 14/129,257 filed on Dec. 24, 2013, the content of which is hereby incorporated herein in its entirety by reference.

Such U.S. patent application Ser. No. 14/129,257 is a national phase filing under 35 C.F.R. § 371 of and claims priority to PCT Patent Application No. PCT/NZ2012/000168, filed on Sep. 20, 2012, which claims the priority benefit under 35 U.S.C. § 119 of New Zealand Patent Application No. 595367, filed on Sep. 23, 2011, the contents of each of which are hereby incorporated herein in their entireties by reference.

FIELD

This invention relates to a compliance monitor. In particular, the invention relates to a compliance monitor for monitoring patient usage of a medicament delivery device. The invention may be particularly suitable for use with metered medicament inhalers, for example, those used for the treatment of respiratory diseases such as asthma, COPD, cystic fibrosis, bronchiectasis, and so on.

BACKGROUND

The use of medicament inhalers for the treatment of respiratory diseases is well known.

A common type of medicament inhaler is what is known as a pressurised Metered Dose Inhaler (pMDI). Such inhalers generally comprise a medicament canister and an actuator.

The medicament canister contains medicament under pressure and is designed to deliver a metered dose of medicament in the form of an aerosol spray.

The actuator comprises a substantially L-shaped hollow tube which has a first open end adapted to receive the medicament canister, and a second open end which acts as a mouth piece.

Medicament canisters for use with a pMDI generally have a spray stem extending from one end which is adapted to engage with a spray-directing element housed within the actuator, and adjacent to the mouth piece of the actuator. When the canister is pushed down into the actuator, the spray stem and spray-directing element combine to direct a metered dose of medicament out through the mouthpiece and into the mouth of the user (or into a spacer or other holding chamber, prior to being inhaled by the user).

Another common type of medicament inhaler is what is known as a Dry Powder Inhaler (DPI). DPI's are generally in the form of a disc or grinder (similar to a pepper grinder) which may be rotated in order to dispense a metered dose of dry powder into an appropriate receptacle or mouthpiece, from where it may then be inhaled by the user (for example, by sucking strongly on the mouthpiece of the actuator).

Some medicament inhalers are kept on hand for use in a specific event or emergency. For example, if a person were to have a sudden asthma attack, they may reach for a medicament inhaler which contains what is generally known as a "reliever" medicament. A reliever medicament is fast acting and in most cases will relieve (or reduce the severity of) the asthma attack, almost instantaneously.

Other medicament inhalers are designed for regular use in order to prevent an event such as an asthma attack and/or to manage or control a disease such as asthma. Such inhalers are generally known as "preventers" because the regular use of such inhalers serves to prevent (or minimise the likelihood of) an asthma attack. The regular use of preventer medicament by asthma sufferers is generally effective in controlling the disease and/or preventing the vast majority of asthma attacks. Commonly, preventer medicament for asthma sufferers is taken twice a day, usually at a set time in the morning and in the evening.

There are now also available "combination" medicament inhalers which combine both a reliever and preventer medicament, with a view to both controlling the respiratory disease (with the preventer medicament), when a patient uses their reliever medicament for symptom alleviation.

A problem or difficulty associated with the use of medicament inhalers generally is poor medicament compliance, particularly in relation to the use of preventer medicament inhalers. That is, many studies have shown that users frequently do not take their medicament at the predetermined or prescribed times and/or in the required amounts. This is a particular problem amongst young children, the elderly, or people with intellectual disabilities.

The consequences of this non-compliance are reduced disease control, lower quality of life, lost productivity, hospitalisation and avoidable deaths.

Not only is compliance to preventative medicaments typically low, but it has also been shown that actual compliance by a user is lower than the same user's estimated compliance.

In order to address the issue of poor medicament compliance, there are available a number of compliance monitoring devices for use with medicament inhalers.

Virtually all compliance monitoring devices incorporate dose counting means. In a general sense, dose counting means provide the simplest embodiment of a compliance monitor, as the dose count may indicate the number of medicament doses delivered and/or the number of medicament doses remaining in the medicament inhaler (the latter known as "absolute dose counters"). The doses dispensed or remaining may also be displayed on a dosage counter, such as an LCD display, housed on the medicament inhaler. Knowing the number of doses dispensed by, or the number of doses remaining in, the medicament canister is of particular importance to the person using the inhaler because that person will know when they are close to having to replace the canister (and that person will not otherwise go to use the inhaler and unexpectedly find that the canister is empty—with possibly dire consequences). Compliance monitoring devices are available for use with both pMDI's and DPI's.

The earliest dose counting mechanisms for pMDI's usually incorporated mechanical dose counting switch mechanisms such as levers or springs or trigger rods—which were mechanically actuated by movement of the canister within the actuator when a dose of medicament was dispensed. For example, see U.S. Pat. No. 4,817,822 (Rand et al) and U.S. Pat. No. 5,020,527 (Dessertine).

There are several problems associated with the use of such mechanical dose counting means. Firstly, the mechanical switch mechanisms include moving parts which may suffer wear and tear or otherwise deteriorate over time. Secondly, the switch mechanisms could break off and enter the medicament delivery pathway, and be inadvertently swallowed by the user. Thirdly, the mechanical switch mechanisms, which are commonly housed within the actuator tube, can change the airflow characteristics of the inhaler, which may adversely impact on the medicament delivery performance of the inhaler. Lastly, mechanical switch mechanisms may also be inadvertently triggered by the user, for example during washing of the actuator body to clean away any built up medicament residue.

In recognition of some of the above problems or difficulties, U.S. Pat. No. 6,601,582 (referred to herein as "the GSK Patent") describes a mechanical dose counter which is integrally formed on the medicament canister. However, a disadvantage associated with the GSK Patent is that the incorporation of a dose counting mechanism into each and every medicament canister adds cost. Moreover, given that each canister typically contains only one month's supply of medicament, it is economically and environmentally wasteful to supply and then discard such technology with each month's medication.

More recent dose counting mechanisms incorporate electronic counting means. For example, see U.S. Pat. No. 5,544,647 (Jewett et al), U.S. Pat. No. 6,202,642 (McKinnon et al) and US Patent Publication No. 2005/0028815 (Deaton et al).

However, most electronic dose counting mechanisms also rely on the canister physically engaging with a switch mechanism for the purpose of closing an electrical switch (to indicate a dosage count of one). For example, in order to record a dosage count of one, Jewett includes a microswitch (42) which is physically engaged by the leading edge (19) of a sleeve (17) which is attached to the canister (16)—see FIG. 1.

Similarly, Deaton utilises a ramp portion (42) which is physically engaged by the shoulder (26) of the canister (14) during the dispensing of a dose of medicament—see FIGS. 22*a* and 22*b*.

Hence, because such electronic dose counting means also include moving parts, these parts are likewise susceptible to wear and tear and/or deterioration over time (they may also be susceptible to breaking off and/or interfering with the airflow within the inhaler). Furthermore, the use of most electronic dose counters involve having to make modifications to the medicament inhaler, which has the potential to interfere with the correct operation of the inhaler.

Furthermore, the fitting of mechanical or electronic dose counters to an inhaler usually requires modifications to the inhaler, for example the drilling of a hole in the side of the actuator or the attachment of a cap to the canister. The fitting of such dose counters to an inhaler can therefore be a fiddly or time consuming operation.

More importantly however, any modifications made to the actuator (or canister) have the potential to interfere with the airflow characteristics within the actuator, possibly affecting the effectiveness of delivery of a dose of medicament. This may result in the patient not receiving the required amount of medicament in order to treat the disease.

The modifications made to the actuator may also be prone to interference while washing the actuator, which could result in inaccurate dose counting or compliance monitoring (Jewett and Deaton address this issue by housing the compliance monitoring means within a hermetically sealed housing—which increases cost and manufacturing complexity).

Deaton discloses, in FIG. 19, an embodiment where a dome switch 44 is mounted externally on the underside of the mouth piece 18. The user holds the apparatus 10 by putting their thumb on the bottom of the mouth piece 18, and over the switch 44, and squeezes on the top of the canister 14 with their fingers. In the course of this squeezing action, the switch 44 is pressed or closed to thus register the recording of a dose. However a disadvantage associated with this design is that many people, and especially the elderly or very young or people with intellectual disabilities, may not have sufficient strength and/or cognitive abilities to force the canister to dispense a dose by using one hand only. Instead, the canister and the underside of the mouth piece will often be gripped by a finger and thumb of each hand of the person and the canister depressed in such a fashion. This will often result in the switch not being engaged by the person. For example, if each person's thumbs were spaced apart on the underside of the mouth piece, and on each side (rather than on) the dome switch 44, then a dose would not be recorded by the dome switch 44. Hence, the dose counter of Deaton does not allow for all doses of medicament to be recorded regardless of how the user holds and/or operates and/or manipulates the medicament delivery device during the dispensing of each dose of medicament.

Most mechanical or electronic dose counters are designed to be absolute dose counters. That is, when a new medicament canister is placed in the actuator, the counters are either manually or automatically set to the number of doses remaining in the full canister (typically around 120 doses which usually comprises one month's supply of a preventer medicament). The GSK Patent referred to previously describes an example of an absolute dose counter (formed on the canister rather than the actuator).

Every time a dose of medicament is dispensed, the absolute dose counter serves to reduce the displayed number of doses remaining by one. Hence a user is able to keep track of the number of doses remaining in the canister, and can therefore ensure he/she has a replacement canister at hand prior to when the first canister is due to run out.

A disadvantage associated with absolute dose counters is that they are dedicated to only one canister at a time. Hence, they are not able to monitor the ongoing compliance characteristics of a user over a period of time which may involve the user going through many canisters of medicament. For example, absolute dose counters are not able to monitor a person's usage over all four seasons to determine useful information such as any seasonal fluctuations. Absolute dose counters are also not able to monitor the ongoing compliance characteristics of a user should they change medicaments when only half way through an existing canister.

Presently available electronic compliance monitoring devices also include means to record a range of compliance data, in addition to dose counting. For example, Dessertine includes a timer to indicate time between doses. McKinnon includes an electronics module to record date and time as well as more comprehensive patient usage information. McKinnon also describes a means for transmitting this data, either wirelessly or otherwise, to a docking station or device such as a personal computer.

Most electronic compliance monitoring devices are integrally formed with the inhaler, usually by being mounted on, or integrally formed with, the actuator body (eg, see Jewett and Deaton). This presents its own difficulties or limitations.

Firstly, because the compliance monitoring device is integrated with the medicament inhaler, it cannot generally be reused for longer than the life of the inhaler. Compliance monitoring technology, and especially electronic compliance monitoring technology, adds cost when integrated into each and every inhaler. Given that each inhaler typically contains a one month supply of medicament, it is economically wasteful to supply and then discard such technology with each months medication.

However, reusing an actuator over more than one medicament container can lead to residual medicament build-up that reduces the quantity of the drug delivered by the inhaler, and changes the deposition properties of the aerosol particles, meaning patients get less medication.

Furthermore, repeatedly discarding the plastic and electronic compliance monitoring technology also creates an environmental sustainability problem that needs to be addressed (medicament inhalers are produced in their millions and one company alone has produced more than 500 million inhalers). Additionally, as not all disease sufferers exhibit poor disease control or poor compliance, it is wasteful to provide such features embedded into each inhaler of a given type.

Perhaps partly in recognition of the above disadvantages associated with inhalers with integrally formed compliance monitoring means, McKinnon describes an electronics module (116) which is releasably attachable to a sleeve attachment (112) which is fitted to the actuator (104). However, the removal of the electronics module from the sleeve renders the sleeve inoperable, which must then be removed and discarded, which is wasteful and expensive (eg, see Page 12, lines 63-65). Furthermore, the electronics module must be reprogrammed once it has been removed from the sleeve and prior to the module being fitted to another sleeve (eg, see Page 10, lines 56-58). Moreover, the fitting of the sleeve and electronics module to an inhaler is a time consuming and complex operation (eg, see FIGS. 30 & 31 and the related descriptions on Page 13 and 14). This presents significant operational difficulties, especially for young children, the elderly or people with intellectual disabilities. Furthermore, the sleeve (112) is designed for attachment to only one specific brand of actuator (see claim 8). Hence, the McKinnon device cannot be used across a range of different actuators.

U.S. Pat. No. 5,564,414 (Walker et al) describes the concept of a dose counter which is incorporated into a removable sleeve which is designed to fit over and around the body of a manufacturer's inhaler. However, the dose counter utilised by Walker is either an external plunger trigger located on the outside of the sleeve or an internal lever trigger built into the body of the manufacturer's actuator. The former is analogous to fitting a cap to the top of the medicament canister which has the potential to interfere with the airflow characteristics of the medicament inhaler. The latter involves modifications having to be made to the inhaler, specifically the actuator, and also results in moving parts being inside the medicament delivery channel. Furthermore, Walker uses a dose counter with a mechanical counting mechanism (an external or internal trigger mechanism) which therefore has the same disadvantages generally associated with mechanical counting means, as referred to previously.

PCT Patent Application No. PCT/US2008/052869 (Levy et al) describes a sleeve housing (24) which is releasably attachable to an actuator body (12). The sleeve housing includes electronic monitoring apparatus and the device is designed to monitor usage in order to predict an exacerbation event. However, Levy relies on a counting means or dose counter which requires attachment of a cap 28 to the canister (16) which is adapted to engage with a dose-dispensing sensor (26) during the delivery of a dose of medicament. Hence, Levy requires modifications to the inhaler prior to being able to be used—which has the potential, over time, to interfere with the effectiveness of the inhaler to properly deliver medicament. Furthermore, the fitting of dose counting caps to the tops of canisters has the potential to interfere with the airflow characteristics of the medicament inhaler. The fitting of caps also increases the height or length of the inhaler, sometimes quite significantly. This can result in the inhaler being unable to be operated easily by small children, for example due to the child not having large enough hands to grasp both the top of the cap/canister and the bottom of the actuator or attachable housing.

Levy also discloses the use of wireless technology to transmit compliance date to a remote device such as the laptop of a health professional. This data may be transmitted in real time or at predetermined set times. Another patent which discloses the use of wireless technology to transmit data is U.S. Pat. No. 6,958,691 (Anderson et al).

Another disadvantage associated with the releasable housings or sleeves described in McKinnon, Walker and Levy is that they would not be able to be used in relation to a medicament canister already fitted with an absolute dose counter, eg the device described in the GSK Patent referred to previously.

A problem associated with integrated electronic compliance monitoring devices is neatly summarized in U.S. Pat. No. 5,809,997 (Wolf) at Page 2, line 53 onwards. Namely (and to paraphrase), many drugs are regulated and require exact actuator conformity. That is, there should be no modifications made to the actuator structure as any modifications may distort the reliability of the delivery of the medicament. Moreover, physicians, researchers, insurance companies, and so on, would not want to risk (for example, in terms of liability) the possibly of affecting the proper delivery of the medicament through these dedicated electronic instruments without the same assurance of proper drug delivery as with the commercial actuator provided by the drug manufacturer.

Perhaps to partly address these concerns raised in Wolf, and as otherwise outlined above, there is described, in US 2007/0023034 A1 (referred to herein as "Altana"), a compliance monitor 20 in the form of a rubber housing which is releasably attachable to the underside of a pMDI inhaler. The housing includes a battery 24, a switch 26, and an electronics module 28. The switch 26 is designed to be pressed by the thumb of a user when the user ordinarily dispenses a dose of medicament. However, Altana suffers from the same disadvantage as Deaton, as referred to previously. Namely, the switch 26 may not be engaged by the user every time a dose is dispensed, for example if the mouth piece was gripped by both thumbs on either side of the switch 26, a dose would not be recorded. Moreover, if the inhaler was gripped by both hands of the user about half way up the actuator body, and the inhaler subsequently actuated, then the dose would not be recorded—due to the Altana device necessarily requiring that the user place his/her thumb directly over the switch 26 or the flexible portion 38 of the housing 20. Hence, the dose counter of Altana does not allow for all doses of medicament to be recorded regardless of how the user holds and/or operates and/or manipulates the medicament delivery device during the dispensing of each dose of medicament.

Furthermore, the device described in Altana is prone to falling off the mouth piece, for example due to the inhaler being bumped against a surface or perhaps being jostled around inside a person's pocket or bag.

Having regard to the foregoing, it may therefore be of advantage if there was available a compliance monitor for monitoring patient usage of a medicament delivery device which was attachable to a medicament delivery device, without any modifications being required to the medicament delivery device, and which ensured that all doses were counted, notwithstanding the medicament delivery device being held, operated and/or manipulated in different fashions by different users.

Object

It is an object of the present invention to provide a compliance monitor for monitoring patient usage of a medicament delivery device, which goes some way towards addressing some or all of the aforementioned problems or difficulties, or which at the very least provides the public with a useful choice.

Definitions

Throughout this specification unless the text requires otherwise, the word 'comprise' and variations such as 'comprising' or 'comprises' will be understood to imply the inclusion of a stated integer or step or group of integers or steps but not the exclusion of any other integer or step or group of integers or steps.

Throughout this specification, the terms "patient" or "user" or "person" or "patient usage", when used in relation to the use of a medicament delivery device, is to be understood to refer to any person that uses a medicament delivery device.

STATEMENTS OF INVENTION

According to one aspect of the present invention, there is provided a compliance monitor for monitoring patient usage of a medicament delivery device, said medicament delivery device including a store of medicament and a medicament dispensing means, and said compliance monitor including:
   a) a housing adapted to enclose said medicament delivery device,
   b) a dose counter, associated with said housing, for recording the delivery of a dose of medicament to the patient from the medicament delivery device,
      the arrangement and construction being such that said housing is loosely coupled to said medicament delivery device, whereby said housing is able to move relative to said medicament delivery device during the delivery of the dose of medicament, and it is this movement which actuates the dose counter, either directly or indirectly, in order to record the delivery of said dose of medicament.

Preferably, the medicament delivery device may be a metered medicament inhaler, for example a pMDI or a DPI used for the treatment of respiratory diseases such as asthma, COPD, cystic fibrosis, bronchiectasis, and so on. However, it is to be understood and appreciated that the compliance monitor may also be used with other medicament delivery devices, for example insulin delivery devices, syringes, pill boxes or nebulisers.

The device may also be used to monitor patient usage of a reliever medicament in order to determine any potential overuse and/or for predicting a potential exacerbation event, prior to the event occurring.

In one embodiment, the housing may be permanently attached to the medicament delivery device. Any suitable means may be utilised for permanently attaching the housing to the medicament delivery device. In such an embodiment, the medicament delivery device and housing may be manufactured and/or sold as a complete unit.

In another embodiment, the compliance monitor may preferably include a housing which may be releasably attachable to, and/or around, the medicament delivery device.

In such an embodiment, the housing may be provided with a hinged portion, which, when open, allows for the medicament delivery device to be placed within the housing, and which, when closed, serves to retain and/or enclose the medicament delivery device. The hinged portion may be provided with closure and release means, to secure the hinged portion, and release the hinged portion, respectively.

An advantage associated with having a releasably attachable housing is that the compliance monitor may be portable across a range of different medicament delivery devices and/or be reused by the patient. For example, when a medicament delivery device exhausts its supply of medicament, the compliance monitor may be removed from the medicament delivery device and releasably fitted to either another medicament delivery device or to the same medicament delivery device with a replacement supply of medicament added. Hence, the compliance monitor is not thrown out after a medicament delivery device, to which it is attached, has dispensed all of its medicament. This in savings in cost and also results in less waste. Furthermore, any data being collected by the compliance monitor in relation to the patient usage of the medicament delivery device may therefore be continuous over a period of time that may include the patient going through many supplies of medicament (either with the same medicament delivery device or across a range of medicament delivery device and/or medicaments).

The housing may preferably be attachable to the medicament delivery device, and subsequently operable, without any modifications being required to the medicament delivery device. That is, the medicament delivery device simply sits within the housing of the compliance monitor.

A significant advantage of such an arrangement is that the compliance monitor does not in any way interfere with, or otherwise affect, the ability of the medicament delivery device to administer medicament. This compares favourably with the prior art devices referred to previously, most of which require modifications to the medicament delivery device in order to be fitted and/or operable. For example, modifications may include the drilling of a hole into the side of an inhaler or the fitting of a cap to a medicament canister—both of which have the potential to interfere with the airflow characteristics within the inhaler and/or adversely affect the ability of the inhaler to dispense medicament.

Furthermore, the attaching of the housing to or around the medicament delivery device preferably does not require the use of any tools in order to be fitted; instead the medicament delivery device is simply placed within the housing of the compliance monitor.

The housing may be of any suitable size, shape or configuration as required or desired, or as dictated by the type or configuration of the medicament delivery device.

In one embodiment, the housing may be adapted to partially enclose the medicament delivery device.

Preferably however, the housing may fully enclose the medicament delivery device.

The housing may be made of any suitable material although a plastics material may be preferred as it is relatively light, and may be conveniently and inexpensively mass produced, for example by injection moulding technology.

The housing may be substantially opaque, translucent or transparent. For example, and for aesthetic purposes, the housing may be substantially opaque and of the same colour as a particular manufacturer's range of medicament delivery devices to which it is intended to be fitted.

Alternatively, the housing may be substantially transparent (or translucent) so that parts of the medicament delivery device may be inspected or viewed through the housing.

Preferably, there may be a dose counter associated with the housing, for recording the delivery of a dose of medicament to the patient from the medicament delivery device Preferably, the dose counter may be able to monitor the doses dispensed by the medicament delivery device, from a position outside of the medicament delivery device.

Examples of suitable dose counters, or dose counting means, include (but are not limited to): a mechanical switch; an electromechanical switch; an electronic switch; a strain gauge; an optical dose counter; a capacitive monitor (to detect changes in an electric field during the delivery of a dose of medicament); and an inductive monitor (to detect changes in a magnetic field during the delivery of a dose of medicament). Such dose counters, for use with medicament delivery devices, are common to the prior art and will be well known by those skilled in the art, and it is not intended therefore to describe each in any great detail herein.

Preferably, the arrangement and construction of the compliance monitor is such that the housing may be loosely coupled to the medicament delivery device, whereby the housing is able to move relative to the medicament delivery device during the delivery of the dose of medicament, and it is this movement which actuates the dose counter, either directly or indirectly, in order to record the delivery of the dose of medicament.

In such an embodiment, the substantially loose fit of the housing with respect to the medicament delivery device may serve to ensure that the dose counter records every dose of medicament dispensed by the medicament delivery device, regardless of how the patient holds and/or operates and/or manipulates the medicament delivery device during the dispensing of a dose of medicament.

In one embodiment, the movement of the housing relative to the medicament delivery device, during the delivery of the dose of medicament, may be primarily in a longitudinal direction with respect to (longitudinal axis of) the medicament delivery device.

In another embodiment, the movement of the housing relative to the medicament delivery device, during the delivery of the dose of medicament, may be primarily in a transverse direction with respect to the medicament delivery device.

In yet another embodiment, the movement of the housing relative to the medicament delivery device, during the delivery of the dose of medicament, may be in both a longitudinal and transverse direction with respect to the medicament delivery device.

In one embodiment, the compliance monitor may further include a sensor(s) for detecting whether the medicament delivery device was positioned correctly, with respect to the patient's body, at the time the dose of medicament was dispensed. For example, the sensor may include a temperature sensor for sensing the temperature of the mouth of the patient (for use with a medicament inhaler), or a proximity sensor for detecting the proximity of the body of the patient (for example, during the use of a nebuliser or syringe).

In one embodiment, the compliance monitor may further include a detection means for detecting when the store of medicament is inserted into, and/or removed from, the medicament delivery device. For example, the compliance monitor may utilise an optical sensor or a switch mechanism (preferably electronic) for such detection purposes.

Preferably, the housing of the compliance monitor may further include an electronics control module (ECM), with the ECM preferably being in electronic communication with the dose counter.

Preferably, the compliance monitor and/or dose counter and/or ECM may be adapted to monitor and/or store information relating to patient usage of the medicament delivery device. This information may also include any type of non-dose counting information relating to the operation of the medicament delivery device and/or patient usage of the medicament delivery device. For example, the ECM may include a real time clock (or be in electronic communication with one) to enable the compliance monitor to record a date and time for each dose of medicament dispensed.

Other information monitored and/or recorded may include (but not be limited to) the following events:

1. When a store of medicament has been removed from and/or placed into the medicament delivery device.
2. When a medicament has been removed from and/or placed into the housing of the compliance monitor.
3. The amount of medicament remaining in the medicament delivery device.

Preferably, the housing may include an output for transferring patient usage data to an electronic device. For example, the output may include an electronic jack or socket (eg, a USB port) for connection by cable to a computer or cell phone.

In another embodiment, the compliance monitor may further include a communications device, for the wireless transmission of patient usage data relating to the patient usage of the medicament delivery device. An example of a suitable communications device is that substantially as described in our NZ Patent No. 575943 (the contents of which are incorporated herein by reference).

The communications device may preferably be able to transmit the patient usage data to a system for managing patient usage data, for example the system substantially as described in our NZ Patent No. 575836 (the contents of which are incorporated herein by reference).

The compliance monitor may include notification means to notify the patient of a particular event. For example, the notification means may include a means for reminding the patient to take a dose of medicament should the ECM determine or receive notification that the patient has not taken a dose within a predetermined time. Likewise, the notification means may be adapted to alert the patient to a situation where they have taken too much of a medicament over a predetermined time period, which may be indicative of an exacerbation event.

The notification means may preferably include, or be in electrical communication with, a visual display and/or an audio output means.

An example of a suitable notification means that may be used with the present invention is that substantially as described in our NZ Patent No. 540250 (the contents of which are incorporated herein by reference).

The compliance monitor may also include an audio sensor to detect sound associated with delivery of a dose of medicament. In such an embodiment, the ECM may be adapted to receive information gathered by the audio sensor, and use this to confirm that a dose of medicament has been dispensed, in conjunction with the recording of the dose by the dose counter. In such an embodiment, the ECM may be configured to only record that a dose has been dispensed when the dose counter and the audio sensor both determine that a dose has been dispensed. That is, if the audio sensor determined that a dose had been dispensed, but the dose counter did not (or vice versa), then a dose may not be recorded.

In one embodiment, the dose counter may operate mechanically, and be in communication with a mechanical display for displaying the number of doses dispensed by, and/or the number of doses remaining in, the store of medicament.

In one embodiment, the dose counter and/or ECM may be housed within a hermetically sealed compartment(s), for example to minimise exposure to dust or medicament particles and/or to enable the compliance monitor to be washed from time to time.

The ECM may preferably include a user interface to allow the patient to access any data recorded or received by the ECM, and/or to change the settings of the device. Preferably, the user interface may include a LCD screen and at least one control button.

The ECM may also preferably include a dose counter display for viewing by the patient, for example on a LCD screen. This LCD screen may be the same as that used with the user interface. In such an embodiment, the dose counter display may temporarily disappear when the patient is using the user interface to change the settings of the compliance monitor, only to reappear once the patient has finished, for example after a predetermined length of time has passed since the user interface was last used.

Alternatively the dose counter display may have its own dedicated display.

The compliance monitor may be used by the patient to serve as an absolute dose counter. In such an embodiment, and for example, the patient may utilise the user interface to choose this option and then enter the total number of doses remaining to be dispensed by the medicament delivery device, this number being displayed by the dose display counter. After the dispensing of each dose of medicament by the medicament delivery device, the dose counter display will reduce the number of doses remaining by one.

The compliance monitor may also be used by the patient to serve as a non-absolute dose counter. In such an embodiment, and for example, the patient may utilise the user interface to choose this option and then reset the dose display counter to zero. After the dispensing of each dose of medicament by the medicament delivery device, the dose counter display will increase the number of doses taken by one. Furthermore, the patient may keep an ongoing total of the number of doses of medicament dispensed over a set period of time, and in relation to a number of different stores of medicament, rather than just in relation to one supply of medicament.

The medicament delivery device may preferably be a medicament inhaler, for example a pMDI or a DPI.

With respect to such a use of the compliance monitor, the housing may include inhalation detection means for detecting whether the patient inhaled the medicament when the medicament was dispensed by the medicament inhaler. Such detection means are common in the prior art and will be well known by those skilled in the art.

The compliance monitor may also be used to monitor patient usage of a reliever medicament in order to determine any potential overuse and/or for predicting a potential exacerbation event, prior to the event occurring.

PREFERRED EMBODIMENTS

The description of a preferred form of the invention to be provided herein, with reference to the accompanying drawings, is given purely by way of example and is not to be taken in any way as limiting the scope or extent of the invention.

DRAWINGS

Figure 2:
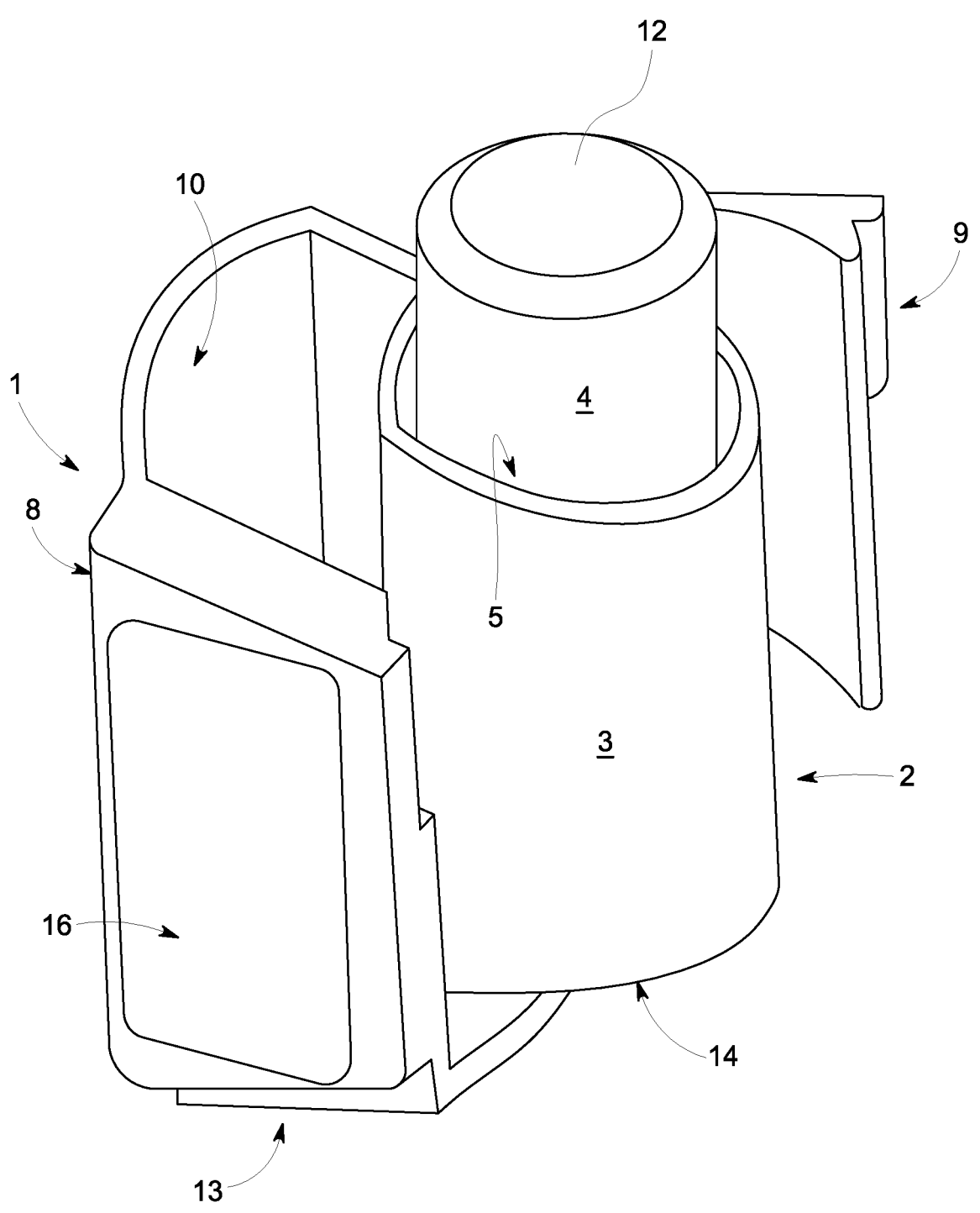
Figure 3:
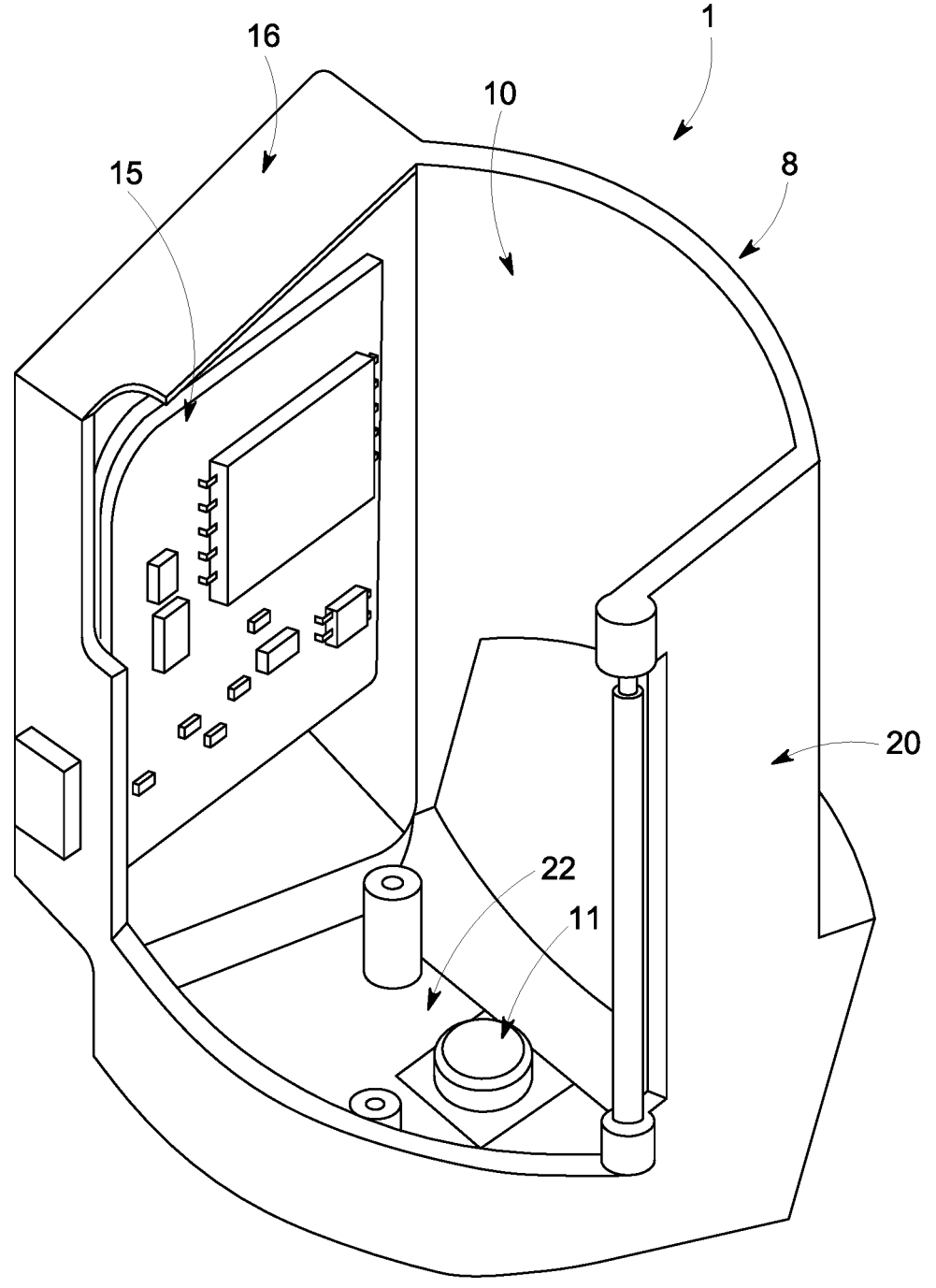
Figure 4:
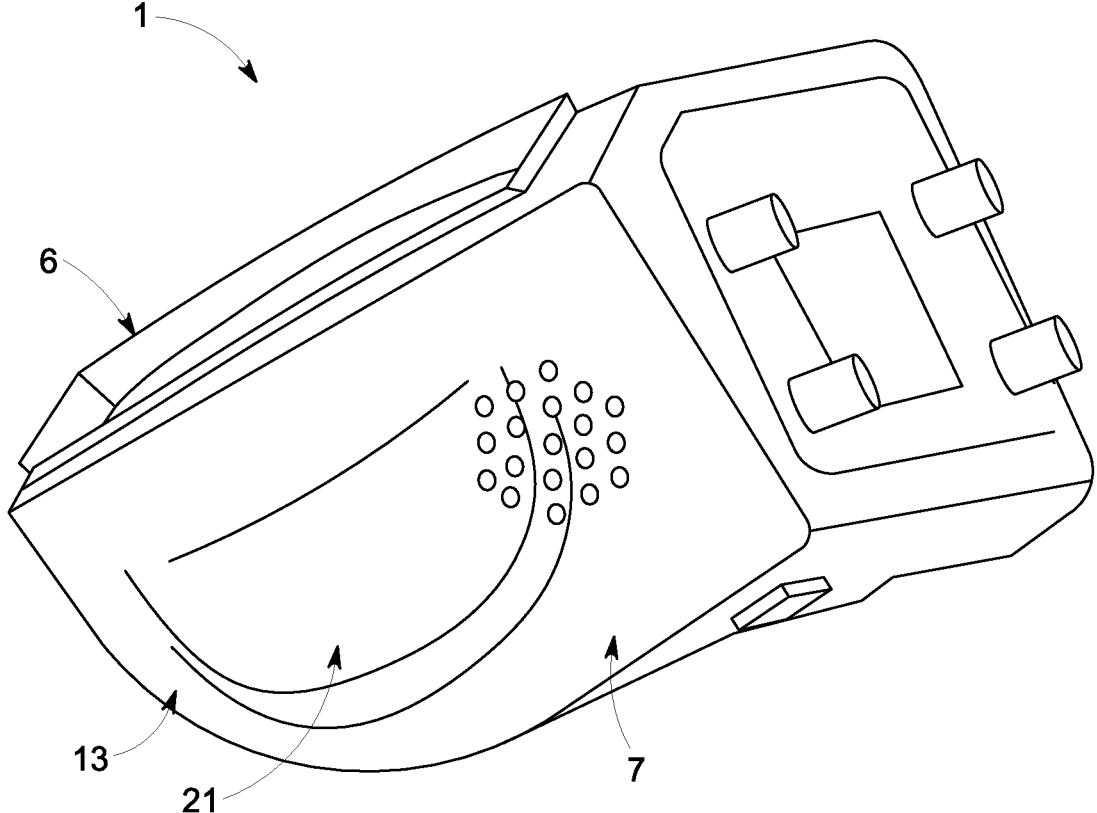

FIG. 1: is a front perspective view of one possible embodiment of a compliance monitor, when fitted to a pMDI, FIG. 2: is a view of the embodiment of FIG. 1, showing how the housing of the compliance monitor is fitted to the pMDI, FIG. 3: is a cut-away view of the housing of the compliance monitors illustrated in FIGS. 1 and 2, and FIG. 4: is an underside view of the compliance monitor illustrated in FIGS. 1-3.

DESCRIPTION OF PREFERRED EMBODIMENTS

Having regard to FIGS. 1 and 2, there is shown a compliance monitor, generally indicated by arrow 1. The compliance monitor 1 is used for monitoring patient usage of a pMDI, generally indicated by arrow 2.

The pMDI 2 includes an actuator 3 and a medicament canister 4. The actuator 3 comprises a substantially L-shaped hollow tube which has a first open end 5 (See FIG. 2) adapted to receive the medicament canister 4, and a second open end 6 which acts as a mouth piece. The medicament canister 4 has a spray stem (not shown) extending from one end which is adapted to engage with a spray-directing element (not shown) housed within the actuator 3, and adjacent to the mouth piece 6. When the canister 4 is pushed down into the actuator 3, the spray stem and spray-directing element combine to direct a metered dose of medicament out through the mouthpiece 6 and into the mouth of the user (or into a spacer or holding chamber, from which it is inhaled by the user).

The compliance monitor 1 includes a housing, generally indicated by arrow 7, for releasable attachment to the pMDI 2. The housing 7 is adapted to fully encircle or enclose the pMDI 2, as shown The housing 7 is comprised of an injection moulded plastics material and is substantially opaque in appearance.

With respect to FIG. 2, the housing 7 includes a main body portion 8 and a hinged door-type portion 9.

The hinged portion 9 in FIG. 2 is shown in an open position which allows the actuator 3 to be placed into the interior 10 of the main body portion 8. Once the actuator 3 has been placed in the main body portion 8, the hinged portion 9 is closed, as shown in FIG. 1. The hinged portion 9 is releasably secured to the main body portion 8 by the use of a latch (not shown).

Having regard to FIG. 3, there is shown an electronic dose counter 11 associated with the housing 7, in the form of a pressure operated, electronic switch 11. The switch 11 is located between the inner surface 22 of the underside 13 of the housing 7 and the outer surface 14 of the underside of the actuator 3.

The arrangement and construction of the compliance monitor 1, with respect to the pMDI 2 is such that the housing 7 is loosely coupled to the pMDI, whereby the housing 7 is able to move relative to the pMDI during the delivery of a dose of medicament from the pMDI, and it is this movement which causes the switch 11 to engage with, or abut, the outer surface 14 of the underside of the actuator 3, thus actuating the electronic dose counter (pressure sensitive switch) 11 in order to record the delivery of the dose of medicament.

This arrangement is best illustrated in FIG. 1. That is, the housing 7 in FIG. 1 has a gap 17 above the mouthpiece 6 and a gap 18 below the mouthpiece 6. These gaps 17, 18 are each approximately 2-3 mm (although a smaller or larger gap may be used). This provides for a certain degree of movement of the housing 7 with respect to the actuator 3 (in a substantially longitudinal direction with respect to the longitudinal axis of the pMDI 2). This loose fit, or degree of movement, has the effect of ensuring that the switch 11 is actuated every time a dose of medicament is dispensed, regardless of whether the person's fingers or thumbs are directly over the underside of the switch 11. This is because the movement of the housing 7, during the time the pMDI 2 is being actuated, serves to ensure that the switch 11 will abut, or engage with, the outer surface 14 of the underside of the actuator 3, thus actuating the switch 11 and therefore recording or registering the dose count.

For example, when a patient wishes to dispense a dose of medicament from the pMDI 2, they will usually place a finger (or fingers) on the top 12 of the canister 4 and a thumb (or thumbs) on the underside 13 of the housing 7 and force the canister down in order to release a dose of medicament through the mouthpiece 6 and into the mouth of the user. This action has the effect of forcing the patient's thumbs up and against the underside 13 of the housing 7 where the switch 11 is located, and this results in the pressure sensitive switch 11 being forced against the outer surface 14 of the underside of the actuator 3, regardless of whether the person's fingers or thumbs are directly over the underside of the switch 11, or otherwise.

Furthermore, the compliance monitor 1 would also record a dose being dispensed even if the patient placed their finger(s) on the top 12 of the canister 4 and their thumbs along each side 20 of the housing 7, and then depressed the canister 4. This is because the housing 7 would still move relative to the pMDI 2, resulting in the pressure sensitive switch 11 still being forced against the outer surface 14 of the underside of the actuator 3, thus actuating the switch 11 and therefore recording or registering the dose count.

Hence, the compliance monitor 1 allows for the dose counter 11 to record every dose of medicament dispensed by the pMDI 2, regardless of how the patient holds and/or operates and/or manipulates the pMDI 2 during the dispensing of a dose of medicament. This is due to the loose fit of the housing 7 with respect to the pMDI 2.

This configuration has advantages over the prior art devices disclosed in Deaton (with respect to the embodiment illustrated in FIG. 19 of Deaton) and Altana. This is because both of these prior art devices describe fixed housing and they would not register a dose count in situations where the person's thumbs were spaced apart on the underside of the actuator when a dose is dispensed or if the patient gripped the sides 20 of the pMDI with their thumbs instead of the underside 13 of the housing 7 (because in these instances, there would be no pressure between the dose counting switch and the actuator, when the dose was dispensed).

Hence, the substantially loose fit of the housing 7 with respect to the pMDI 2 serves to ensure that the dose counter 11 records every dose of medicament dispensed by the pMDI 2, regardless of how the patient holds and/or operates and/or manipulates the pMDI 2 during the dispensing of a dose of medicament.

FIG. 4 is view of the underside 13 of the housing 7. As may be seen, the underside 13 of the housing 7 includes a small compartment or a slightly raised portion 21 which accommodates the switch 11 on the inside surface 22 of the housing 7.

It may be also appreciated that the housing 7 is releasably attachable to the actuator 3, and subsequently operable, without any modifications being required to the actuator 3. Moreover, the pMDI 2 may be operated as normal once contained within the compliance monitor 1. There are also no moving parts such as trigger rods or springs which may break off or which may deteriorate over time or which may otherwise interfere with the normal operation of the pMDI.

Furthermore, and as may also be seen from the drawings, the attaching of the housing 7 to or around the actuator 3 does not require the use of any tools in order to be fitted; instead the pMDI 2 is simply placed within the main body 8 of the housing 7, and the hinged door 9 is then closed and secured.

Moreover, the compliance monitor 1 includes a dose counting means 11, which is able to monitor the doses dispensed by the pMDI, from a position outside of the inhaler.

The compliance monitor 1 includes an electronics control module 15 (ECM) housed within a compartment 16, which forms part of the housing 7. The ECM 15 is in electronic communication with the switch 11, and is adapted to monitor and/or store information relating to patient usage of the pMDI 2. Examples of the type of information that may be monitored and/or stored by the ECM 15 have been previously described in this specification. Furthermore, we also refer you to our NZ Patent No. 574666 which describes a different housing for a medicament inhaler, but which describes at length the types of functions that may be undertaken or performed by the ECM 15. Hence the contents of NZ Patent No. 574666 are incorporated herein by reference.

Other features that the compliance monitor 1 may include (but which are not illustrated) are as follows:

1. A sensor(s) to for detecting whether the pMDI 2 was positioned correctly during delivery of a dose of medicament. For example, the mouthpiece 6 may include a temperature sensor for determining the temperature associated with the proximity of a user's mouth around the mouthpiece 6 during the dispensing of a dose of medicament. If the user's mouth is not detected then the ECM may not record or register a dose having been successfully administered, notwithstanding if the switch 11 has recorded a dose being dispensed.
2. A detection means for detecting when the canister 4 is removed from, or placed into, the actuator 3.
3. A detection means for detecting when the hinged door 9 is opened and/or closed.
4. A detection means for detecting when the pMDI 2 is placed within and/or removed from the housing 7.
5. A detection means for determining the amount of medicament remaining in the medicament delivery device.
6. An output for transferring or downloading the patient usage data to a docking station and/or to an electronic device such as a laptop, computer, iPad® or mobile electronic phone or device.
7. A reusable and portable communications device, substantially as that described in our NZ Patent No. 575943, for the wireless transmission of patient usage data relating to the patient usage of the medicament delivery device. Furthermore, the communications device may be able to transmit the patient usage data to a system for managing patient usage data, substantially as described in our NZ Patent No. 575836.

8. A notification means to notify the patient of a particular event, for example, the notification means substantially as described in our NZ Patent No. 540250.

9. An audio sensor(s) to detect sound associated with the dispensing of a dose of medicament, for example an audio sensor in the mouthpiece of the actuator 3 or adjacent where the spray stem of the canister 4 engages with the spray-directing element of the actuator 3. If the expected audio is not detected then the ECM may not record or register a dose having been successfully administered, notwithstanding if the switch 11 has recorded a dose being dispensed.

An advantage associated with the compliance monitor 1 is that it may function as both an absolute dose counter with respect to the current canister of medicament 4 as well as a non-absolute dose counter, for example for a length of time covering the use of many canisters 4. Hence, the patient may obtain two useful sets of data—one relating to the patient usage in relation to each canister 4 of medicament, and the second relating to general usage information over a significant (or predetermined) length of time.

It will be appreciated that another advantage associated with the device 1 generally is that it may serve as both a patient compliance monitor (for example to monitor patient compliance in relation to a medicament such as a preventer or combination medicament) and also as a device to monitor patient usage of an emergency drug such as a reliever. The patient (or a third party such as a parent or medical practitioner) may therefore obtain important and useful information relating to a patient's compliance generally, as well as the ability to be forewarned of the possibility of an event such as an exacerbation event.

The invention may be particularly useful for use with large clinical trials, for example those used to determine whether a particular medicament may have unwanted side effects. Such trials may include a number of people in a trial group (those using the medicament being tested) and a number of people in the control group (those not using the medicament being tested). There may be upwards of 3000 people in each group, and the results of the clinical trail may be very important. Hence, it is imperative that the people running the trial know for certain whether the trial group and/or control group has been taking the medicament as prescribed, and over the set time period of the trial (which may be many months), and regardless of how they use or manipulate the pMDI during the dispensing of a dose of medicament. Furthermore, because the present invention is reusable in relation to each new container of medicament being tested, it may be used by each patient in the trial, for the entire duration of the trial.

The invention may also be useful as a diagnostic tool by a respiratory specialist for use with their patients. For example, a specialist may be unsure whether a patient has asthma or heart disease. The specialist may therefore supply the device to a patient for use with asthma medicament over a period of time and the usage information being used by the specialist to diagnose the disease. Moreover, the patient may return the device to the specialist at the conclusion of the trial, whereby it may be supplied the next patient of the specialist.

The invention may also be useful as a self diagnosis device for a patient. That is, a patient may use the device to self-monitor their own personal usage and make conclusions or changes as a result. Alternatively, it may be used by a parent or care giver as a tool for ascertaining if someone in their care has been taking their medicament correctly, or otherwise.

This may be of particular advantage during clinical trials where the ongoing monitoring of a patient is being undertaken over a considerable time period, and perhaps whereby the patient changes medication half way through the trial.

Variations

While the embodiments described above are currently preferred, it will be appreciated that a wide range of other variations might also be made within the general spirit and scope of the invention and/or as defined by the appended claims.

We claim:

1. A compliance monitor for monitoring patient usage of a medicament delivery device, said medicament delivery device including a store of medicament and an actuator, and the compliance monitor including:
   a housing adapted to enclose said medicament delivery device,
   a dose counter, associated with said housing, for recording the delivery of a dose of medicament to a patient from the medicament delivery device,
   said housing is loosely coupled to said medicament delivery device, whereby said housing is able to move relative to said medicament delivery device during the delivery of the dose of medicament, and such movement is configured to actuate the dose counter, either directly or indirectly, in order to record the delivery of said dose of medicament; and
   a detector that is configured to detect when the store of medicament, of the medicament delivery device, is inserted into and/or removed from the housing,
   the housing including:
   a main body portion, and
   a door, the door movably attached to the main body portion, and
   the door being movable between an open position and a closed position, and wherein the door, when open, allows for the medicament delivery device to be placed within and removed from the main body portion; and
   wherein the housing includes:
   the main body portion having an aperture defined therein and through which a mouthpiece, of the medicament delivery device, extends such that the mouthpiece, of the medicament delivery device, protrudes from the aperture to deliver the medicament directly to the patient.

2. The compliance monitor of claim 1, the detector including an optical sensor.

3. The compliance monitor of claim 1, the detector including a switch mechanism.

4. The compliance monitor of claim 1, the detector including at least one sensor.

5. The compliance monitor of claim 1, further including a sensor that is configured to detect whether the medicament delivery device was positioned correctly, with respect to the patient, at the time the dose of medicament was dispensed.

6. The compliance monitor as claimed in claim 1, wherein the medicament delivery device is a medicament inhaler.

7. The compliance monitor as claimed in claim 6, wherein said medicament inhaler is a pressurized metered dose inhaler.

8. The compliance monitor as claimed in claim 1, wherein said housing further includes an electronics control module (ECM), said ECM being in electronic communication with said dose counter.

9. The compliance monitor as claimed in claim 8, wherein said ECM is adapted to monitor and/or store patient usage data relating to patient usage of said medicament delivery device.

10. The compliance monitor as claimed in claim 9, wherein said housing includes an output for transferring said patient usage data to an electronic device.

11. The compliance monitor as claimed in claim 9, the store of medicament includes a canister with the medicament inside the canister.

12. The compliance monitor of claim 1, wherein the door is attached to the main body portion by a hinge, such that the door is a hinged door, the hinged door configured to be secured in the closed position.

13. The compliance monitor of claim 1, the door constituting a side of the compliance monitor.

14. A compliance monitor for monitoring patient usage of a medicament delivery device, said medicament delivery device including a store of medicament and an actuator, and the compliance monitor including:

a) a housing adapted to enclose said medicament delivery device, b) a dose counter, associated with said housing, for recording the delivery of a dose of medicament to a patient from the medicament delivery device, said housing is loosely coupled to said medicament delivery device, whereby said housing is able to move relative to said medicament delivery device during the delivery of the dose of medicament, and such movement actuates the dose counter, either directly or indirectly, in order to record the delivery of said dose of medicament; and the compliance monitor further including a detector that detects when the store of medicament, of the medicament delivery device, is inserted into and/or removed from the housing; and the housing including a main body portion and a hinged door, the hinged door hinged to the main body portion, and the hinged door being movable between an open position and a closed position, and the hinged door, when open, allows for the medicament delivery device to be placed within the housing;

wherein the housing includes:

the main body portion having an aperture defined therein and through which a mouthpiece, of the medicament delivery device, extends such that the mouthpiece, of the medicament delivery device, protrudes from the aperture to deliver the medicament directly to the patient.

15. The compliance monitor of claim 14, the compliance monitor further including a latch, the latch provided to secure the hinged door in the closed position, to secure the medicament delivery device within the housing.

\* \* \* \* \*